United States Patent [19]
Holroyd

[11] Patent Number: 5,388,549
[45] Date of Patent: Feb. 14, 1995

[54] MILKING SAMPLING FOR DIAGNOSTIC PURPOSES

[75] Inventor: Michael Holroyd, Royston, Great Britain

[73] Assignee: R J Fullwood & Bland Limited, Shropshire, England

[21] Appl. No.: 104,789

[22] Filed: Aug. 10, 1993

[51] Int. Cl.$^6$ .............................................. A01J 3/00
[52] U.S. Cl. .................................................. 119/14.14
[58] Field of Search ............... 119/14.14, 14.02, 14.01, 119/14.08

[56] References Cited
FOREIGN PATENT DOCUMENTS
2354820 11/1974 Germany .
2231658 11/1990 United Kingdom .

Primary Examiner—Gene Mancene
Assistant Examiner—Thomas Price
Attorney, Agent, or Firm—Lee, Mann, Smith, McWilliams, Sweeney & Ohlson

[57] ABSTRACT

Methods and apparatus enabling a diagnostic test to be carried out on milk flowing in a milk line from an animal being milked, without interrupting the milking process, in which a portion of the milk is diverted through a by-pass in which an extracting means (14) in the form of a vacuum-operable pump and timer acts to separate from the milk flowing in the by-pass a milk sample and to deliver said sample through an associated sampling valve (16) to a testing device (18).

10 Claims, 6 Drawing Sheets

MILKING SAMPLING FOR DIAGNOSTIC PURPOSES

FIELD OF THE INVENTION

This invention relates generally to milk sampling for diagnostic purposes, and more specifically to a method and apparatus for extracting a sample of milk to be tested from the milk line in a milking system, whilst substantially avoiding interruption of the routine milking procedure.

BACKGROUND TO THE INVENTION

Milking of an animal is effected by means of a claw having attached thereto cups which are connected to the animals teats. In the mechanised situation which exists in a milking installation, a milk line connects to the claw to receive the milk. In order to draw off the milk, a constant vacuum of about 0.5 Bar is applied to the milk line, switchable on and off by a valve. The vacuum is switched on prior to commencement of milking and connects the cups to the teats. After milking has been completed, the vacuum is switched off. A second vacuum system provides a pulsating vacuum to the outside of the liners, to stimulate milk flow and maintain blood circulation in the teats. It will be understood, therefore, that in the environment of a milking installation, there are generally available two sources of vacuum namely a constant or steady vacuum and a pulsating vacuum.

The Invention

According to one aspect of the present invention, there is provided a method of extracting a sample of milk from a milk line to which a vacuum is applied, for extracting milk from an animal, according to which a portion of the milk is a milk/air mixture flowing in the milk line is diverted through a by-pass, in which is provided an extraction means operable by at least one of a fixed vacuum and a pulsating vacuum for separating from the milk flowing in the by-pass a sample thereof and delivering it to a testing device.

The said extraction means may also serve to control activation of the testing device for the purpose of testing the extracted milk sample.

Initiation of an operating cycle to the sample extracting means may be effected manually.

Preferably, in an upstream part of the sample extracting means, the milk flowing in the by-pass is raised to a pressure slightly above atmosphere pressure. This is desirable in order to cause the sample of milk to be delivered to the testing device, notwithstanding the vacuum which is apppplied to said by-pass to cause milk to be drawn through the milk line when said means is not delivering a sample.

Preferably, the operating cycle of the sample extracting means is timed, and milk is delivered to the testing device only for a portion of said operating cycle. Thus, according to another aspect of the invention, there is provided a method of extracting a sample of milk from a milk line to which a vaccuum is applied for extracting milk from an animal, according to which a portion of the milk flowing in the milk line is diverted through a by-pass, in which is provided an extraction means operable by at least one of a fixed vacuum and a pulsating vacuum for separating a sample from the milk flowing in the by-pass and delivering the sample to a testing device, the extraction means being operable over an operating cycle which is timed. When the sample extracting means also controls activation of the testing device, the latter may be activated for a subsequent portion of the operating cycle.

Preferably, at the junction where the by-pass connects to the milk line, the line is so formed as to produce a reservoir of milk. In this way a constant flow of milk is generated through the by-pass.

In a preferred method, at a delivery device from which milk is delivered to the testing device, when the delivery device is restored to open the by-pass to a through flow of milk, a temporary inflow of air through the delivery device caused by the vacuum applied in the by-pass, cleans the delivery device of residual milk.

Preferably, when the milk line is cleaned by flushing with cleaning fluid following the completion of a milking operation, the cleaning fluid also passes through the by-pass to clean the sample extracting means and delivery device.

The invention also relates to sample extracting apparatus for carrying out the above described method.

According to another aspect of the invention there is provided apparatus for extracting a sample of milk from a milk line to which a vacuum is connectable, the milk line in use being connected to an animal being milked, comprising a sample extracting means for passing a flow of milk received from the milk line, said means comprising a pump for pressurizing milk and for operating a timer, and a sampling valve receiving the pressurized milk and for delivering a sample of milk to a diagnostic testing device, said sampling valve being operable under control of the timer.

Preferably the milk pump and the sample valve are vacuum operated.

Where a pulsating vacuum is available, the milk pump may to advantage be operated by the pulsating vacuum, whilst the sampling valve is preferably operated from a source of steady vacuum.

The testing device may also be an actuable device for carrying out the diagnostic test, and this device also may be operable by a steady vacuum under control of the timer.

If desired a plurality of testing devices for carrying out different diagnostic tests may be similarly operated and controlled.

One such diagnostic test may be a test for progesterone content of the milk.

A preferred pump is single acting reciprocating pump. The linear stroke of the pump piston is preferably converted to a rotary movement by a suitable transmission device, for example a double-ratchet mechanism which indexes a gear wheel on both the forward and reverse strokes of the pump.

In a preferred embodiment, the timer is driven by the transmission device through reduction gearing. In the timer, one or more timing cams are driven through a clutch, such as a wrap spring clutch, which includes a manually operable release, e.g. a pawl. When the pawl is released, as by a push-button, an operating cycle is initiated during which the timing cam or cams are permitted to perform one complete revolution. A camming surface on one of the timing cams mechanically controls a valve which opens a steady vacuum to the sampling valve for a portion of the operating cycle, thereby diverting the pressurized flow of milk through the sampling device to the testing device. During a later portion of the operating cycle, a camming surface on another timing cam may in similar manner cause activation of the testing device. Except when the sampling valve is operated, milk flows through the pump and the sampling valve. Thus, when the milk line is flushed following a milking operation, cleaning fluid also flows through the sampling means.

In a preferred sampling system, the sampling means is connected as a by-pass to a primary milk line. Preferably, at the junction where the by-pass joins such milk line, a collector is provided in the milk line to collect and retain a reservoir of the flowing milk. In this way, milk flows continously through the by-pass, even though the primary milk line is erratically passing a flow of milk, froth and air.

DESCRIPTION OF EMBODIMENTS

The method and apparatus in accordance with the invention are exemplified in the following description, making reference to the accompanying drawings, in which.

Figure 1:
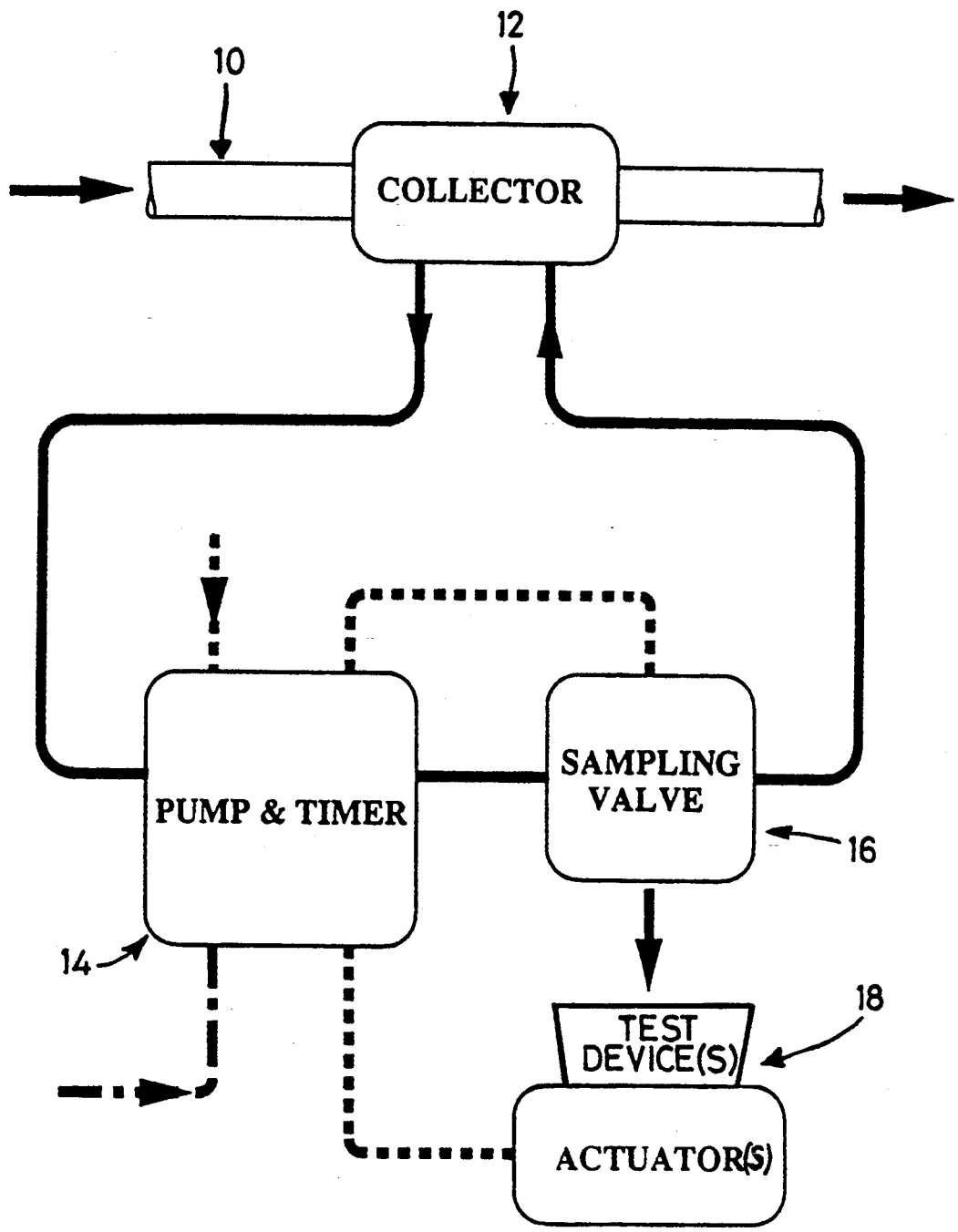
FIG. 1 is a block diagram of a sampling system.

Referring to FIG. 1, the sampling system is connected to a milk line 10 to which a vacuum is applied during milking and through which, in use, is flowing milk being collected from an animal being milked. In fact, in use the line 10 is passing a mixture of milk, froth and air.

The sampling system is in the form of a by-pass connecting to the milk line at a collector 12, which is simply a portion fitted into the milk line having a depressed base, so as to form a reservoir for milk. By virtue of the collector 12, milk flows through the sampling system in the form of a continous stream.

In addition to the collector 12, the sampling system includes a pump and timer unit 14 and a sampling valve 16. An actuable testing device 18 may also be regarded a part of the system. In FIG. 1, the solid black line indicates milk flow, the dotted line indicates an applied fixed vacuum, and the dash-dotted line indicates an applied pulsating vacuum.

A pulsating vacuum is applied to operate the pump and timer unit. The timer controls the application of a steady vacuum for operating the sampling valve and the testing device.

Figure 3:
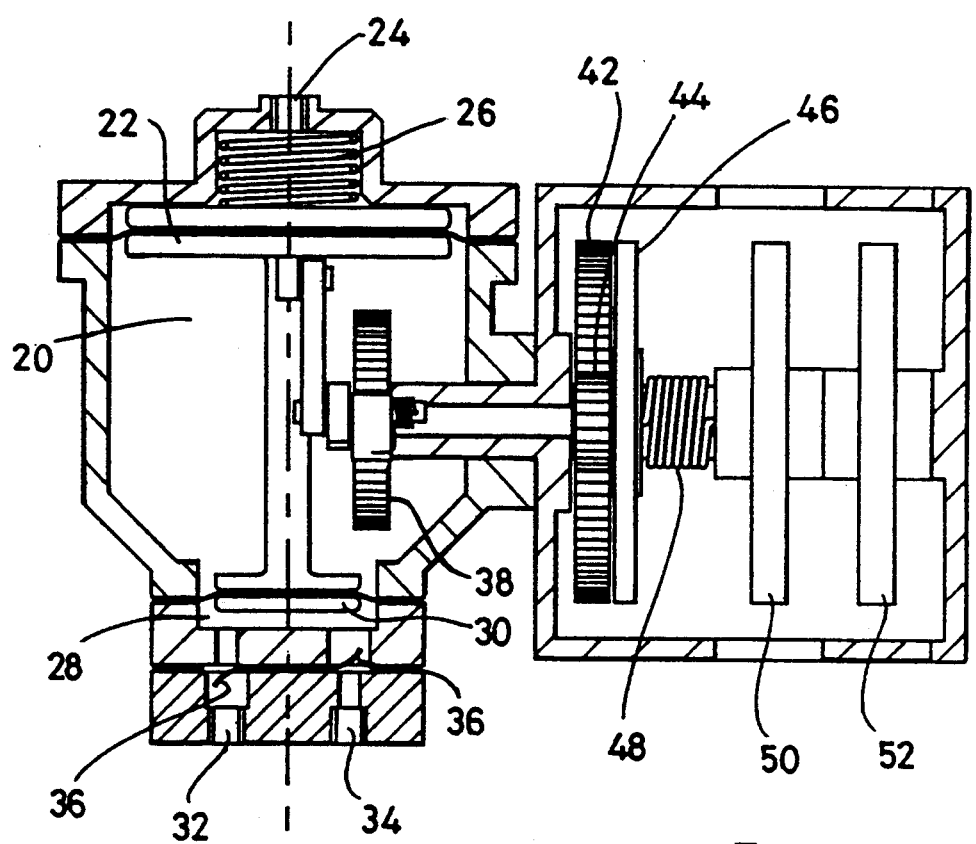

The pump and timer unit 14 as depicted in FIG. 3 comprises a pump on the left-hand side and a timer on the right-hand side. The pump comprises an upper chamber 20 in the upper part of which reciprocates a diaphragm-supported piston 22 under the action of a pulsating vacuum applied at the inlet port 2 4 and of a return spring 26.

The pump also has a lower chamber 28 in which reciprocates a diaphragm-supported secondary piston 30. The lower chamber has a milk inlet 32 and a milk outlet 34, each associated with a one-way valve 36, whereby milk entering the pump, under the influence of the vacuum applied to the milk line, is raised in pressure to slightly above atmospheric pressure. The pressurized milk then passes to the sampling valve 16.

Figure 4:
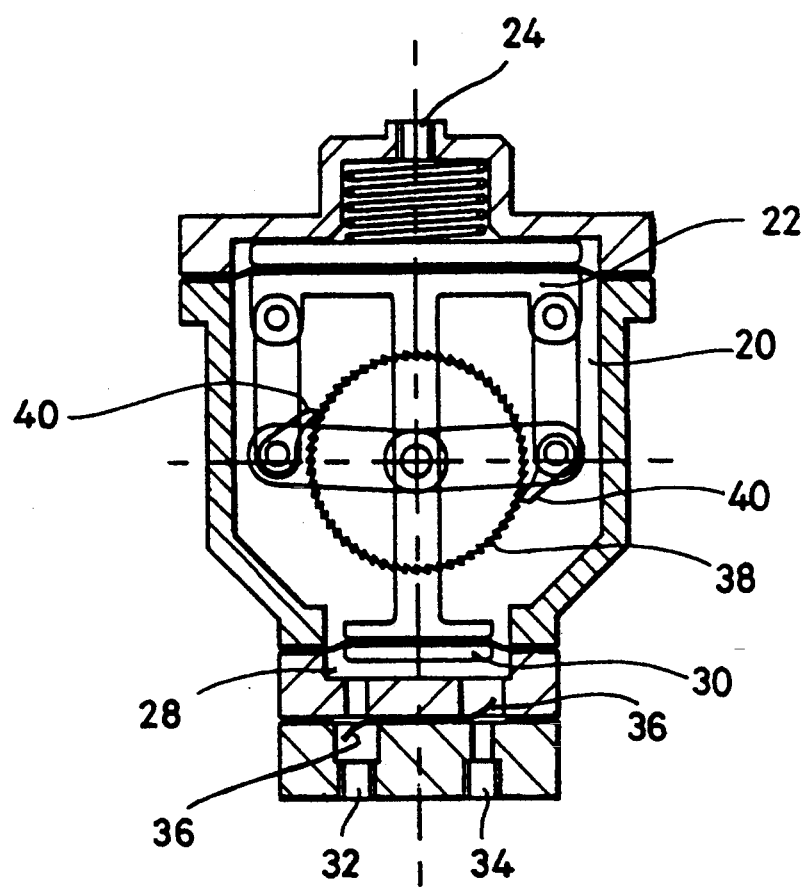
FIG. 4 shows a detail of the pump and timer unit.

As shown in FIG. 4, the piston 22 in the upper chamber 20 drives a double ratchet mechanism in the form of gear wheel 38 and oppositely acting pawls 40, whereby the linear motion of the piston is converted into a stepped rotary movement of the gear wheel. The gear wheel 38 drives the timer. Thus, reverting to FIGS. 2 and 3, the gear wheel 38 couples, through reduction gearing 42, 44 with a disc 46 forming part of a wrap spring clutch 48 carried by a shaft on which are also mounted two timing cams 50, 52. The camming surface 54 on one of these cams is visible in FIG. 2.

The wrap spring clutch also includes a pawl 56 normally engaging with a step in the periphery of the disc 46, therby to prevent rotation of said disc, whereby the timing cams are also held against rotation. However, the pawl 56 can be lifted by, for example, a manually depressed push-button 58, thereby causing the clutch spring to tighten and, start an operating cycle of the timer in which one complete revolution of the shaft carrying the disc and the timing cams takes place. In practice, such an operating cycle occupies about 300 strokes of the pump, taking about 5 minutes.

Figure 2:
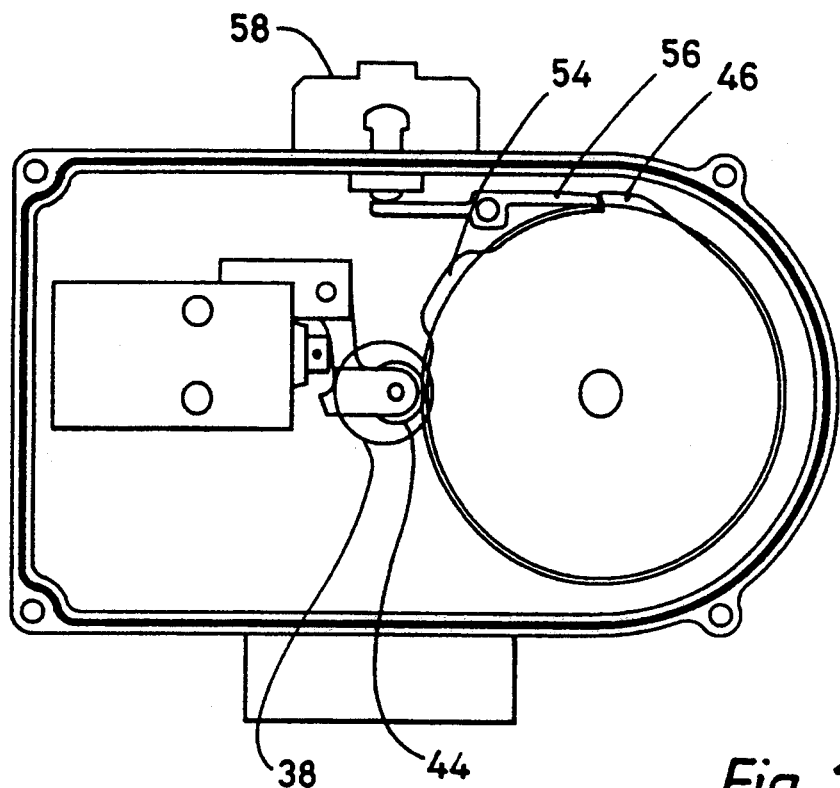
FIGS. 2 and 3 show a sampling pump and timer unit respectively in two side views.

The timing cams mechanically control two valves, one of which is shown in FIG. 2, one controlling application of the steady vacuum to the sampling valve 16 and one controlling application of the steady vacuum to the testing device 18.

Figure 5:
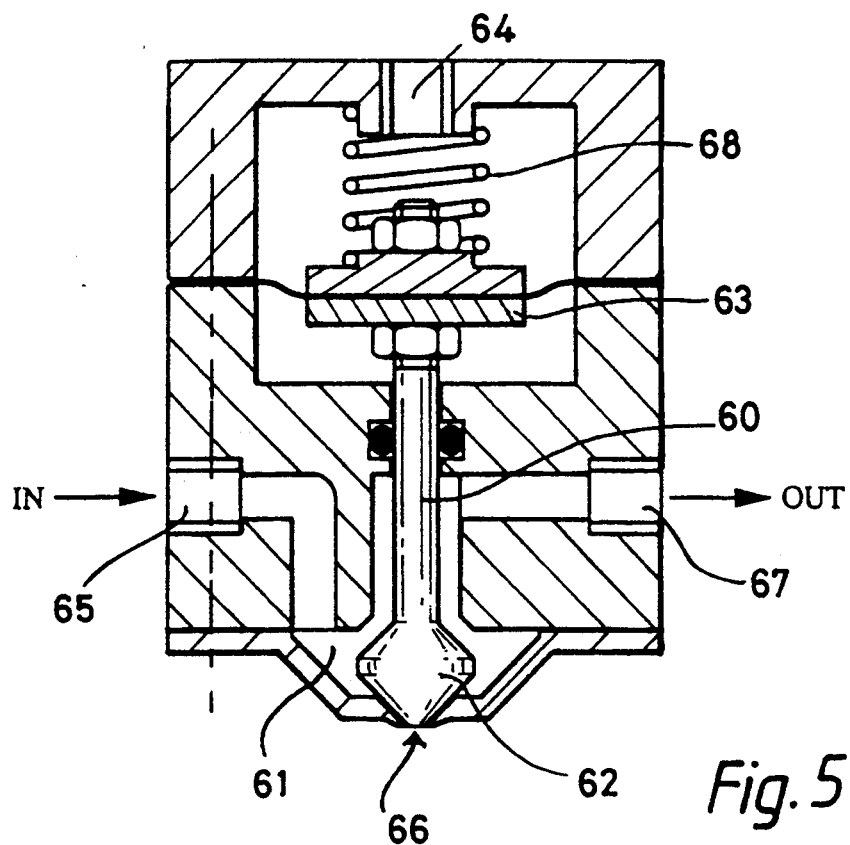
FIGS. 5 and 6 show a sampler valve, respectively in non-operated and operated conditions.
Figure 6:
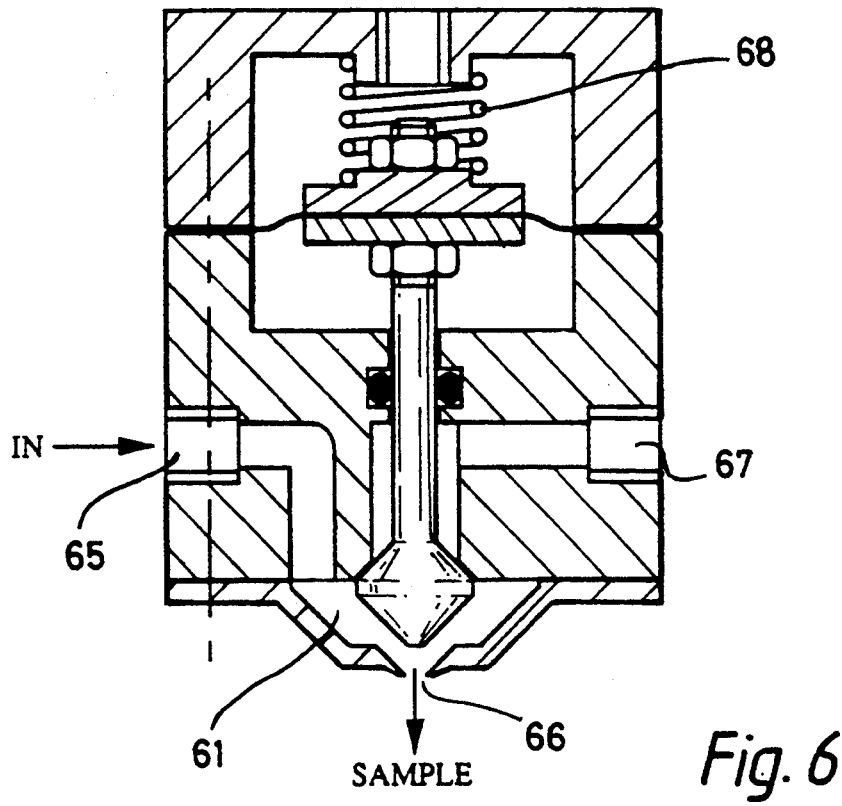

The sampling valve is shown in FIGS. 5 and 6, and comprises a valve member 60 having a head 62 in a milk chamber 61 which passes milk received from the pump, the milk entering at port 65 and leaving at port 67. The valve member 60 is operable by movement of a diaphragm acting thereon via member 63. Thus, when the timing cam 50 causes the steady vacuum to be applied at the inlet port 64, the valve member 60 is lifted for a short period during which a sample of milk is delivered from outlet 66, from the milk chamber, to the testing device. When the steady vacuum is withdrawn from the inlet port 64, spring 68 returns the valve member to the closed position.

It is to be noted that, except when the valve member is operated, there is a through-flow of milk through the milk chamber back to the milk line so that the milk delivered to the testing device is representative of the milk flowing through the milk line at that instant. It also follows that, when the system is flushed with cleaning fluid after completion of a milking Operation, the sample valve is also washed clean. Moreover, when the valve member is restricted to close the milk sample outlet, a momentary back surge of air occurs through said outlet, due to the applied vacuum in the milk line, which sucks any milk clinging to the mating surfaces of the valve member and valve seat back into the milk chamber.

Figure 7:
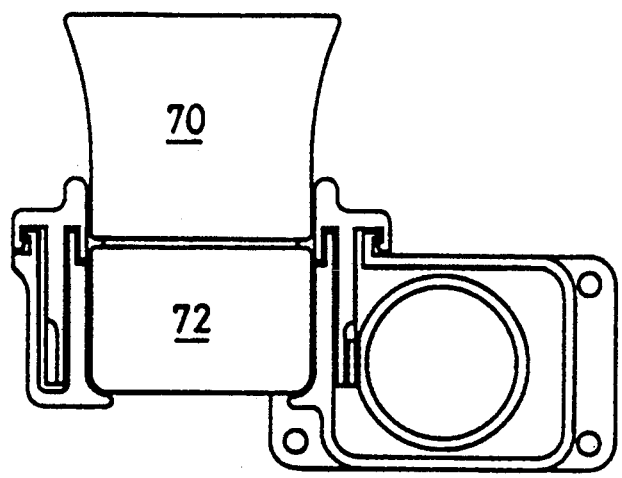
FIGS. 7 and 8 show an actuable testing device, respectively in elevated and plan views.
Figure 8:
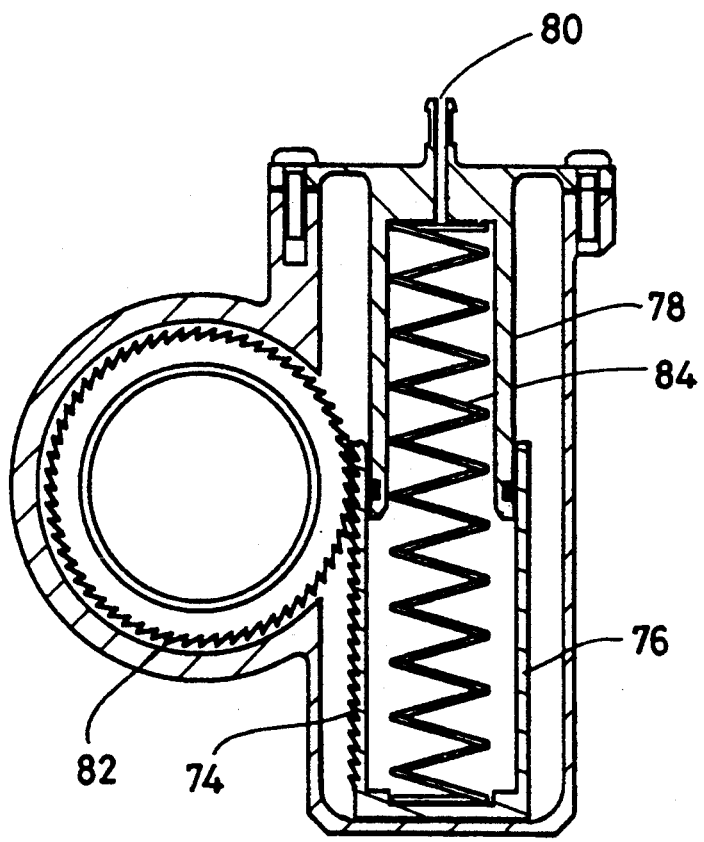

The diagnostic testing device per se forms no part of the present invention. As illustrated in FIGS. 7 and 8, however, it comprises upper and lower relatively rotatable cups, respectively 70 and 72, with openings in the base of the upper cup which can be aligned with or closed off from reagent chambers in the lower cup. The milk sample is retained in the upper cup until the cups are relatively rotated to release some of the milk sample into the reagent chambers.

Relevant to the present invention is the actuator means for effecting the necessary relative rotation of the cups. This occurs after the milk sample has been delivered to the upper cup from the sampling valve, which is ensured by appropriate positioning of the camming surface on the timing cam 52 relative to that of the camming surface in the timing cam 50 which controls the sampler valve.

As shown in FIG. 8, in particular, the actuator means comprises a ratchet 74 on a cylindrical member 76 which is sealingly slideable relative to a fixed cylindrical member 78 under the influence of the steady vacuum, when applied at inlet port 80. Ratchet 74 drives a gear 82 carried by the rotatable cup. Restoration of the member 76 is by means of an internal spring 84.

It will be appreciated that, by providing more timing cams on the timer of FIGS. 2 and 3, it is possible to actuate more than one actuable testing device, for carrying out different diagnostic tests, or to actuate a testing device requiring more than one actuation.

Various modification of the above-described and illustrated arrangement are possible within the scope of the invention hereinbefore defined. In particular, for carrying out the method generally illustrated in FIG. 1, various other constructions of pump, timer and sampling valve, operable by steady and/or pulsating vacuum, may be employed.

Figure 9:
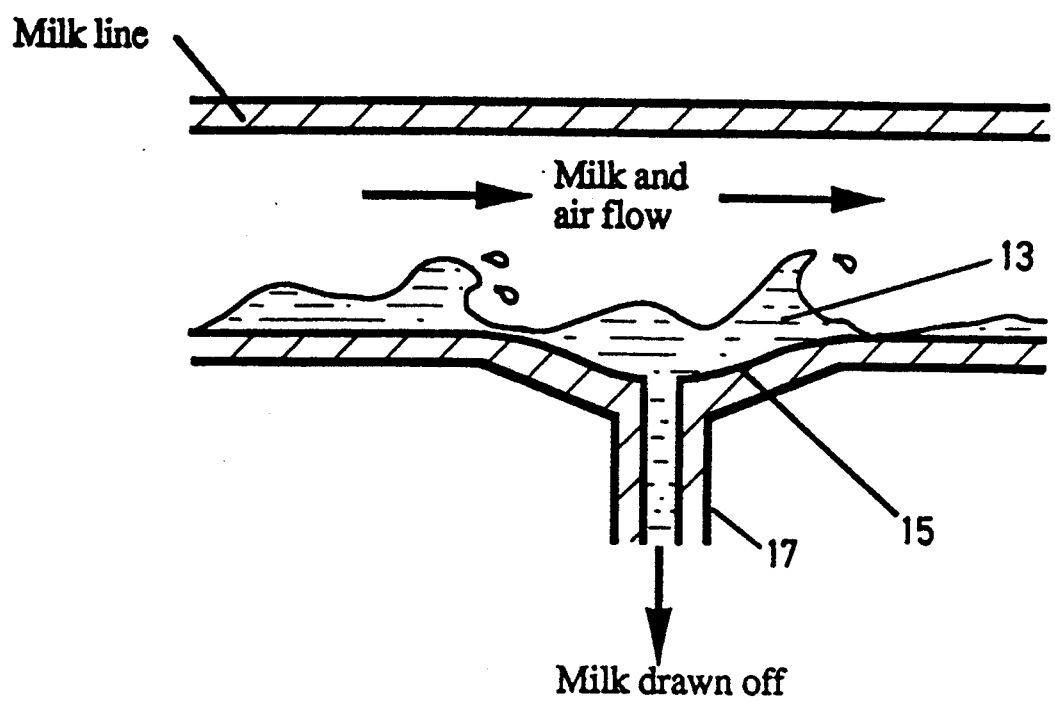
FIG. 9 illustrates the milk collector of FIG. 1.

FIG. 9 illustrates the milk collector 12 of FIG. 1. Milk 13 collects in the depression 15 and is drawn off along tube 17 to the pump and timer unit 14.

I claim:

1. Apparatus for extracting a sample of milk from a milk line to which a vacuum is connectable, the milk line in use being connected to an animal being milked, comprising a sample extracting means for extracting a flow of milk from the milk line, said means comprising a pump for pressurizing milk, a timer associated with the pump, and a sampling valve for receiving the pressurized milk and for delivering a sample of milk to a diagnostic testing device, said sampling valve being operable under control of the timer.

2. Apparatus according to claim 1, wherein the milk pump and the sampling valve are vacuum operated.

3. Apparatus according to claim 2, wherein the milk pump is operated by a pulsating vacuum, whilst the sampling valve is operated from a source of steady vacuum.

4. Apparatus according to claim 1, wherein said diagnostic testing device is an actuable device which is operable by a steady vacuum under control of the timer.

5. Apparatus according to claim 1, including a plurality of testing devices for carrying out different diagnostic tests.

6. Apparatus according to claim 1, wherein the diagnostic testing device is a device for testing the progesterone content of the milk.

7. Apparatus according to any of claim 1, wherein the pump is single acting reciprocating pump.

8. Apparatus according to claim 7, wherein the pump has a linear stroke which is converted to a rotary movement by a transmission device in the form of a double-ratchet mechanism which indexes a gear wheel on both a forward and reverse strokes of the pump.

9. Apparatus according to claim 8, wherein the timer is driven by said transmission device through a reduction gearing.

10. Apparatus according to claim 9, wherein the timer comprises at least first and second timing cams driven through a clutch which includes a manually operable release means for initiating an operating cycle during which said timing cams are permitted to perform one complete revolution, in the course of which a camming surface on said first timing cam mechanically controls a valve which opens a steady vacuum to the sampling valve for a portion of the operating cycle, a camming surface on said second timing cam in similar manner causing activation of the diagnostic testing device.

* * * * *